US006580067B1

(12) United States Patent
Yamada et al.

(10) Patent No.: US 6,580,067 B1
(45) Date of Patent: Jun. 17, 2003

(54) SAMPLE ANALYZING MONITOR AND COMBUSTION CONTROL SYSTEM USING THE SAME

(75) Inventors: Masuyoshi Yamada, Ichikawa (JP); Yuichiro Hashimoto, Kokubunji (JP); Minoru Sakairi, Tokorozawa (JP); Yasuaki Takada, Kiyose (JP); Masami Sakamoto, Hitachinaka (JP); Tomoyuki Tobita, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 71 days.

(21) Appl. No.: 09/712,132

(22) Filed: Nov. 15, 2000

(30) Foreign Application Priority Data

Nov. 19, 1999 (JP) ............................................ 11-329277

(51) Int. Cl.⁷ ........................ H01J 49/00; B01D 59/44; G01N 30/90; G01N 33/487
(52) U.S. Cl. ...................... 250/281; 250/288; 73/19.02; 73/53.01
(58) Field of Search ................................ 250/281, 288, 250/289; 73/19.02, 53, 53.01

(56) References Cited

U.S. PATENT DOCUMENTS

| 3,624,710 A | * | 11/1971 | Carter et al. ................ 73/19.02 |
| 4,234,549 A | * | 11/1980 | Stanley et al. ............. 423/245.3 |
| 5,101,105 A | * | 3/1992 | Fenselau et al. ............. 250/281 |
| 5,612,534 A | | 3/1997 | Mimura et al. ............. 250/281 |
| 5,703,360 A | * | 12/1997 | Fischer et al. ............ 250/252.1 |

FOREIGN PATENT DOCUMENTS

| DE | 19956466 | 8/2000 |
| JP | 4-161849 | 6/1992 |
| JP | 5-312796 | 11/1993 |
| JP | 7-85834 | 3/1995 |
| JP | 7-155731 | 6/1995 |
| JP | 9-15229 | 1/1997 |
| JP | 9-55185 | 2/1997 |
| JP | 9-243601 | 9/1997 |
| JP | 2000-162189 | 6/2000 |
| RU | 2091789 | 9/1997 |
| WO | 97/23779 | 7/1997 |
| WO | 99/13492 | 3/1999 |

OTHER PUBLICATIONS

BUNSEKI, 1998, pp. 512–519.
Hanai et al, "Automatic Analysis of Chlorobenzenes in the Exhaust Gas from MSW Incineration Plant", Bulletin of Institute of Environmental Science & Technology of Yokohama National University, vol. 18, 1992.
K. Hiraoka, "Fundamentals of Chemical Ionization", Mass Spectroscopy, vol. 28, No. 3, Sep. 1980, pp. 185–209.
T.B. McMahon et al, "Intrinsic Acidities of Substituted Phenols and Benzoic Acids Determined by Gas–Phase Proton–Transfer Equilibria", Jounral of the American Chemical Society, vol. 99, No. 7, 1997, pp. 2222–2230.

* cited by examiner

Primary Examiner—Jack Berman
Assistant Examiner—K Fernandez
(74) Attorney, Agent, or Firm—Mattingly, Stanger & Malur, P.C.

(57) ABSTRACT

The present invention is to provide a monitoring device making it possible to measure the concentration of a target trace gas which has an ionization efficiency changed by the affect of impurities and which is absorbed on a pretreatment portion or piping, at a high accuracy and at real time, by adding an internal standard having a known concentration to the target trace gas.

The concentration of the target trace gas is measured while an internal standard having substantially the same properties (such as ionization efficiency change and vapor pressure) as the target trace gas is added. The ion strengths of the target trace gas and the internal standard are compared to calibrate the concentration of the target trace gas.

According to the present invention, the concentration of the target trace gas in gas containing impurities can be online measured at a real time and at high accuracy while being continuously calibrated.

5 Claims, 13 Drawing Sheets

FIG.4A
FIG.4B
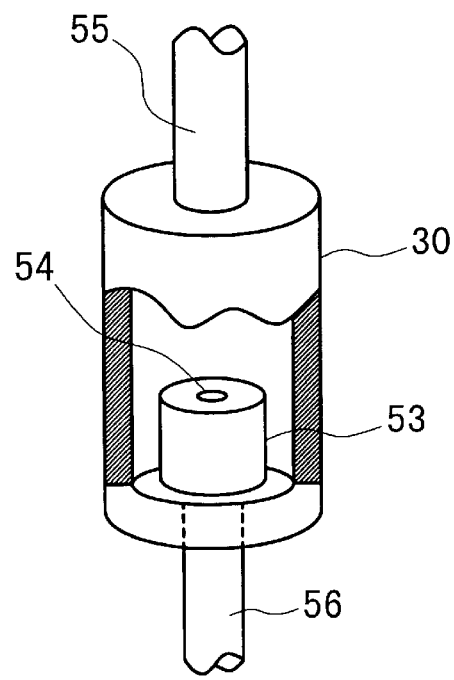
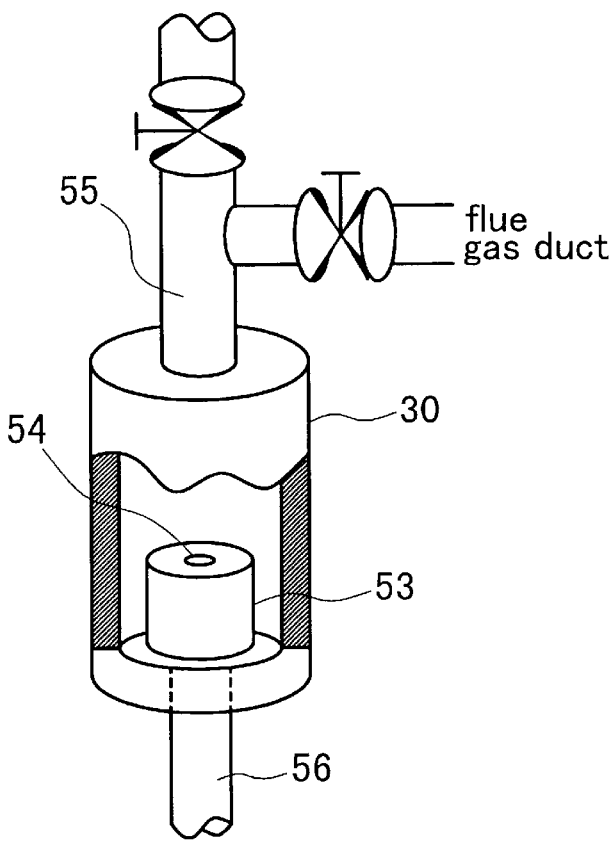

SAMPLE ANALYZING MONITOR AND COMBUSTION CONTROL SYSTEM USING THE SAME

TITLE OF THE INVENTION

Sample analyzing monitor and combustion control system using the same.

BACKGROUND OF THE INVENTION

1. Field of the Invention

The present invention relates to an calibrating process for analyzing a sample and a device therefor, and particularly to a sample analyzing monitor in which dioxin and related compounds contained in combustion flue gas resulting from incineration of non-industrial waste and industrial waste, exhaust gas from metal refining processes, exhaust gas from cars, or the atmosphere are detected to determine the concentration of the dioxins or the dioxin precursors in the flue gas or the atmosphere; and a combustion control system in which the results from the monitoring by means of the monitor are used for combustion control.

2. Description of the Related Art

It is known that dioxins are contained in exhaust gas from metal refining processes, exhaust gas from cars, or waste liquid from a bleaching process of pulp or the like. The word "dioxins" is a general term of polychlorinated dibenzo-p-dioxins (PCDDs) having 75 kinds of isomers and polychlorinated dibenzofurans (PCDFs) having 135 kinds of isomers. A broad sense of the word includes coplanar polychlorinated biphenyl (coplanar PCBs). Dioxin and compounds related thereto are abbreviated to "dioxins congeners" hereinafter.

Findings on the mechanism of generation of dioxin congeners have been accumulated (BUNSEKI, 1998, pp. 512–519). Conditions for generating dioxin congeners varies greatly, dependently on sites, the mechanism of the generation thereof and so on, and are highly complicated. It is considered that in a combustion process at high temperature in an incineration plant or the like, de novo synthesis is an influential mechanism of generation of dioxin congeners. In the de novo synthesis, a chloride of a metal such as cobalt, iron or copper in fly ash functions as a catalyst so that carbon reacts with chlorine. In the basic reaction of the de novo synthesis, carbon atoms, chlorine atoms and oxygen atoms which coexist at high temperature are subjected to radical reaction so that not only dioxin congeners but also many organic chlorine compounds such as polychlorinated benzene congeners and polychlorinated phenol congeners are produced. The produced polychlorinated benzene congeners and polychlorinated phenol congeners turns to precursor congeners of dioxin congeners. It is said that the precursors turn to dioxin congeners. It is also said that in an incineration plant, dioxin congeners are generated mainly by two processes. One thereof is a process in which dioxin congeners are generated upon imperfect combustion inside a combustion furnace, the combustion temperature of which is lower than 800° C. The other is de novo synthesis inside a boiler or a dust collector at a temperature of 250–550° C.

Various measures are taken to reduce the generation of dioxin congeners in incineration plants as much as possible. To suppress the discharge of dioxin congeners to surroundings, it is desired that combustion conditions are improved or techniques for removing dioxin congeners efficiently are developed. However, much time and labor have been required for the development of the techniques for suppressing the discharge of dioxin congeners. For example, the following process has been conducted: the process of combusting wastes under a certain condition, determining the concentration of dioxin congeners in flue gas or fly ash under this condition, obtaining a correlation between the combustion condition and the amount of the generated dioxin congeners, and searching an optimal combustion condition or an optimal removal condition from the correlation.

In order to monitor the operation situation of actual incineration plants, there has been recently suggested a process in which the concentration of dioxin congeners, which have a very low concentration, is not directly measured but an alternative substance which has a relatively high concentration is assayed and then the concentration of the dioxin congeners is estimated from the result of the assay. Examples of such a technique include processes and devices disclosed in the Bulletin of Institute of Environmental Science & Technology of Yokohama National University (Vol. 18, 1992), JP-A-Nos. 4-161849, 5-312796, 7-155731, 9-015229 and 9-243601.

In the techniques disclosed in the Bulletin of Institute of Environmental Science & Technology of Yokohama National University (Vol. 18, 1992) and JP-A-Nos. 4-161849 and 5-312796, polychlorinated benzene congeners are measured by gas chromatography (GC) and are used as an index of alternatives of dioxin congeners. The dioxin congeners are estimated from the correlation between the two.

In the technique disclosed in JP-A-7-155731, dioxin congeners and so on contained in combustion ash are thermally decomposed by heating the ash, so as to reduce the dioxin congeners and so on. Polychlorinated benzene congeners and polychlorinated phenol congeners in the ash before and after the heating are analyzed to estimate the elimination ratio of the dioxin congeners. In this manner, the condition for the thermal decomposition is optimized.

In the technique disclosed in JP-A-9-015229, the concentration of polychlorinated benzene congeners in flue gas and that of polychlorinated phenol congeners therein are measured and then the concentration of dioxin congeners is calculated from a dust concentration and flue gas retention time which are measured in another way and the above-mentioned concentrations.

In the technique disclosed in JP-A-9-243601, polychlorinated benzene congeners and polychlorinated phenol congeners in flue gas are subjected to real-time measurement, and the concentration of dioxin congeners is continuously obtained. The flue gas is introduced to a laser ionizing mass spectrometer to ionize the flue gas. The flue gas is subjected to mass spectrometry. Thus, the concentrations of the polychlorinated benzene congeners and the polychlorinated phenol congeners are obtained. At last, the concentration of the dioxin congeners is indirectly calculated.

JP-A-9-55185 discloses a manner of calibrating the concentration of dioxin congeners in the case that the effect of impurities having a high concentration or measuring conditions such as ionization voltage are changed at the time of analyzing a sample continuously for a long time.

It is expected that the generation of dioxin congeners from incineration plants is reduced by a dioxin-reducing manner based on improvement in combustion conditions, adoption of a removal technique, or the like. However, it is indispensable to measure, at a real time, how much dioxin congeners are reduced by such a dioxin-reducing manner. From such a viewpoint, the above-mentioned methods have the following problems.

Each of the Bulletin of the Institute of Environmental Science & Technology of Yokohama National University (Vol. 18, 1992) and JP-A-Nos. 4-161849 and 5-312796 discloses a manner of analysis, but does not disclose any specific technique for measuring polychlorinated benzene congeners or the like quantitatively. This technique is essential for such monitoring.

JP-A-7-155731 does not disclose any specific technique for measuring polychlorinated benzene congeners, polychlorinated phenol congeners or the like quantitatively. The technique disclosed in JP-A-9-015229 does not have a clear basis of a relationship equation between dioxin congeners and polychlorinated benzene congeners, polychlorinated phenol congeners or the like, which is a premise of the invention. Moreover, this publication does not disclose any specific technique for analyzing these substances quantitatively.

JP-A-9-243601 suggests a possibility of real-time measurement of the concentration of polychlorinated benzene congeners, but does not disclose any specific manner for measuring this concentration.

In JP-A-9-55185, a sample used for concentration-calibration is a material which is the same as a target trace gas. For the calibration, therefore, it is indispensable to stop the introduction of a sample of the target trace gas. Thus, JP-A-9-55185 does not disclose any technique in which an analysis step and an calibration step are simultaneously performed. JP-A-9-55185 also have a problem that in the case of measuring a minor constituent gas in flue gas by mass spectrometer, the mass spectrometer is affected by impurities such as hydrogen chloride, sulfur oxide and nitrogen oxide present in the flue gas so that ionization efficiency changes; and a problem that the target trace gas to be measured adheres to laying pipes from an inlet to a mass spectrometer or a filter so that the concentration of the target trace gas near the inlet becomes different from the concentration thereof introduced to the mass spectrometer.

BRIEF SUMMARY OF THE INVENTION

An object of the present invention is to provide a process and a device making it possible to measure the concentration of a target trace gas in gas containing various impurities while the concentration is calibrated moment by moment and to realize a real-time analysis at a high precision on line.

The present invention has been made to attain the above-mentioned object. The present invention relates to a process in which as a calibration means in an online monitor using mass spectrometry, a material having substantially the same ionization efficiency as a target trace gas, for example, a stable and rare isotope of the target trace gas is added, as an internal standard, at a constant concentration, and then the amount of the ions is measured; and a device therefor.

Specifically, the concentration of the target trace gas is calibrated and quantitatively measured as follows.

(1) An internal standard having properties, such as ionization efficiency and vapor pressure, similar to the target trace gas is introduced at a constant concentration to the side of an incineration furnace of a pretreatment section of a monitor, and then the ion strength ratio of the target trace gas to the internal standard is measured to determine the target trace gas quantitatively.

In this way, it is possible to correct an error resulting from a change in the ion strength on the basis of effects of impurities and an error resulting from a change in the concentration on the basis of adhesion of the target trace gas to pipes in the middle and the pretreatment section. As a result, the target trace gas can be quantitatively measured.

(2) While the amount of waste gas introduced from an incineration furnace to a monitor is monitored to calibrate a change in the amount of an introduced target trace gas based on a change in the amount of the introduced waste gas, an internal standard having properties, such as ionization efficiency and vapor pressure, similar to the target trace gas is introduced at a constant concentration to an ion source of the monitor. In this way, the ion strength ratio of the target trace gas to the internal standard is measured to determine the target trace gas quantitatively.

BRIEF DESCRIPTION OF THE SEVERAL VIEWS OF DRAWINGS

FIG. 4 is a view illustrating an example of an internal standard vaporizer in the present invention.

DETAILED DESCRIPTION OF THE INVENTION

Figure 1:
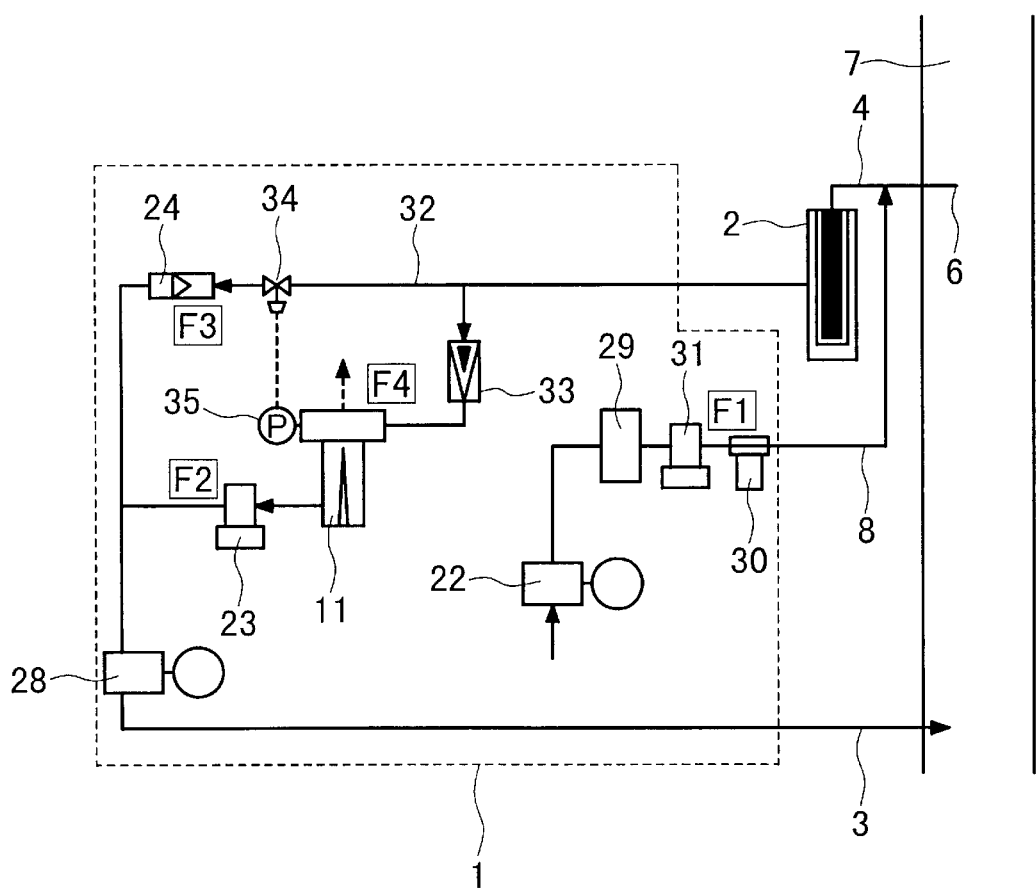
FIG. 1 is a view illustrating a piping arrangement of an embodiment of the present invention.

First, the basis of the present invention will be described. Signal quantity measured with a mass spectrometer used in a monitor unit, that is, ion strength is generally represented by the product of factors expressing the concentration of a sample gas, the ionization efficiency of an ion source, the ion transmission ratio in the mass spectrometer, the detection efficiency therein, and so on.

For example, quantitative analysis of polychlorinated phenol congeners will be described. The same process for quantitative analysis as described below can be applied to the case that materials to be quantitatively analyzed are other materials such as polychlorinated benzene congeners or dioxin congeners.

The concentration $N_{CP}$ of the polychlorinated phenol congeners to be obtained can be basically represented by the summation of concentrations of monochlorophenol (MCP), dichlorophenol (DCP), trichlorophenol (TCP), tetrachlorophenol (TECP), and pentapolychlorinated phenol (PCP). However, monochlorophenol generates no chlorinated a dioxin by condensation reaction. Thus, monochlorophenol is excluded. That is, the concentration $N_{CP}$ to be obtained with a dioxin monitor can be represented as follows:

$$N_{CP} \approx N_{DCP} + N_{TCP} + N_{TECP} + N_{PCP}$$

When flue gas is introduced from a flue gas duct to the monitoring device, absorption of sample molecules in the flue gas to the inner wall of the piping as the duct or desorption thereof from the inner wall comes into question. Therefore, the concentration N depends substantially on the absorption energy Q of the sample molecules, the partial pressure $P_1$ thereof, and the temperature $T_1$ of the piping. In other words, the concentration N is a function of theses factors. Therefore, $N_{CP}(Q, P_1, T_1)$ can be represented as follows:

$$N_{DCP}(Q, P_1, T_1) + N_{TCEP}(Q, P_1, T_1) + N_{TECP}(Q, P_1, T_1) + N_{PCP}(Q, P_1, T_1).$$

Next, the respective concentrations $N_{DCP}$, $N_{TCP}$, $N_{TECP}$ and $N_{PCP}$ will be discussed. In general, ion strength I measured with a mass spectrometer can be represented by the following equation:

$$I(M, P_1, P_2, Q, T_1, T_2) = N(Q, P_1, T_1) \times \alpha(T_2, M, P_2) \times \beta$$

wherein N is the concentration of a sample gas, α is the ionization efficiency of an ion source, and β is the ion transmission ratio in the mass spectrometer, the detection efficiency therein or the like. In this case, a is a function of the temperature $T_2$ of the ion source, α function of the concentration M of interfering components such as hydrogen chloride, and a function of the pressure $P_2$ inside the ion source.

It can be considered that β does not change dependently on the kind of polychlorinated phenols, Accordingly, the ion strengths $I_{DCP}$, $I_{TCP}$, $I_{TECP}$ and $I_{PCP}$ of DCP, TCP, TECP and PCP can be represented by the following formulae, respectively:

$$I_{DCP}(M, P_1, P_2, Q, T_1, T_2) = N_{DCP}(Q, P_1, T_1) \times \alpha_{DCP}(T_2, M, P_2) \times \beta,$$

$$I_{TCP}(M, P_1, P_2, Q, T_1, T_2) = N_{TCP}(Q, P_1, T_1) \times \alpha_{TCP}(T_2, M, P_2) \times \beta,$$

$$I_{TECP}(M, P_1, P_2, Q, T_1, T_2) = N_{TECP}(Q, P_1, T_1) \times \alpha_{TECP}(T_2, M, P_2) \times \beta, \text{ and}$$

$$I_{PCP}(M, P_1, P_2, Q, T_1, T_2) = N_{PCP}(Q, P_1, T_1) \times \alpha_{PCP}(T_2, M, P_2) \times \beta,$$

From the above, the concentration $N_{CP}$ can be represented by the following formula:

$$N_{CP}(M, P_1, P_2, Q, T_1, T_2) \approx$$

$$(I_{DCP}(M, P_1, P_2, Q, T_1, T_2)/\alpha_{DCP}(T_2, M, P_2)$$

$$+I_{TCP}(M, P_1, P_2, Q, T_1, T_2)/\alpha_{TCP}(T_2, M, P_2)$$

$$+I_{TECP}(M, P_1, P_2, Q, T_1, T_2)/\alpha_{TECP}(T_2, M, P_2)$$

$$+I_{PCP}(M, P_1, P_2, Q, T_1, T_2)/\alpha_{PCP}\, T_2, M, P_2)) \times (1/\beta).$$

In this case, the most simple quantitative analysis of the concentration $N_{CP}(M, P_1, P_2, Q, T_1, T_2)$ can be performed as follows.

In the case that polychlorinated phenol congeners which are actually generated from an incineration plant are analyzed, the amount of DCP is 1–20% of the polychlorinated phenol congeners, the amount of TCP is 10–40% thereof, the amount of TECP is 10–40% thereof, and the amount of PCP is small. Therefore, the concentration $N_{CP}$ to be obtained through the dioxin monitor can be represented by the summation of the concentrations of DCP, TCP and TECP.

Actual measurement is made, using a certain material of the piping, under a certain temperature $T_1$ of the piping and a certain temperature $T_2$ of the ion source. Therefore, the concentration $N_{CP}$ is not any function of the temperatures $T_1$ or $T_2$.

In this case, the concentration NCP can be simply represented by the following formula:

$$N_{CP}(M, P_1, P_2, Q) \approx (I_{DCP}(M, P_1, P_2, Q)/\alpha_{DCP}(P_2) + I_{TCP}(M, P_1, P_2, Q)/\alpha_{TCP}(P_2) + I_{TECP}(M, P_1, P_2, Q)/\alpha_{TECP}(P_2)) \times (1/\beta).$$

When an internal standard S having an ionization efficiency ($\alpha_S$) and a concentration ($N_S$) is added to flue gas, the observed ion strength of the internal standard S can be represented under a constant condition by the following formula:

$$N_S(M, P_1, P_2, Q) = (I_S(M, P_1, P_2, Q)/\alpha_S(P_2) \times (1/\beta).$$

Therefore, if the ratio of each of the known concentrations $N_{DCP}$, $N_{TCP}$ and $N_{TECP}$ to the concentration $N_S$ (known concentration) is measured in the range of the concentration to be quantitatively analyzed for polychlorinated phenol congeners (about 0.01–1000 μg/Nm³), the ratio a between the ionization efficiencies can be obtained in a certain constant condition. It can be considered that in this case, the dependency of the ion strength of the sample molecules upon the pressure of the ion source is equal to the dependency of the ion strength of the internal standard molecules upon the pressure of the ion source. Therefore, the ratio between the ionization efficiencies does not depend on the pressure $P_2$. When the sample molecules and the internal standard molecules have substantially the same absorption energy and concentration, it can be considered that the ratio between the ionization efficiencies does not depend on the absorption energy Q and the pressure $P_2$. That is, using the ratios:

$$\alpha_S(P_2)/\alpha_{DCP}(P_2)\ (=k_{DCP}(M)),$$

$$\alpha_S(P_2)/\alpha_{TCP}(P_2)\ (=k_{TCP}(M))\ \text{and}$$

$$\alpha_S(P_2)/\alpha_{TECP}(P_2)\ (=k_{TECP}(M)),$$

the concentration $N_{CP}$ can be finally represented by the following formula:

$$N_{CP}(M) \approx (k_{DCP}(M) \cdot (I_{DCP}(M)/I_S(M)) + (k_{TCP}(M) \cdot (I_{TCP}(M)/I_S(M)) + (k_{TECP}(M) \cdot (I_{TECP}(M)/I_S(M))) \cdot N_S(M).$$

The manner of coping with change in the ionization efficiency or the ion strength by the concentration of interfering components comes into question. If the dependencies of the ion strengths (ionization efficiencies) of the sample molecules and the selected internal standard upon the concentration of the interfering components are substantially the same, the concentration $N_{CP}$ is not any function of the concentration M of the interfering components. For this reason, it is necessary to measure the dependency of the ion strength of each of DCP, TCP, TECP, and the sample used as the internal standard (for example, an organic halogen compound such as dibromophenol) upon the concentration of hydrogen chloride.

When the dependencies of the ion strengths of the sample molecules and the internal standard upon the concentration of the interfering component are substantially the same, the concentration $N_{CP}$ can be represented by the following formula:

$$N_{CP}=(k_{DCP} \cdot I_{DCP}/I_S + k_{TCP} \cdot I_{TCP}/I_S + k_{TECP} \cdot I_{TECP}/I_S) \cdot N_S.$$

In the case that dichlorophenol congeners are actually analyzed quantitatively, the concentration $N_S$ of an internal standard is adjusted in the manner that the internal standard has properties similar to the following: the average amount of dichlorophenol and the average concentration of interfering components such as hydrogen chloride, each of which was beforehand measured in a certain incineration furnace. The ratios $k_{DCP}$, $k_{TCP}$ and $k_{TECP}$ in this case are decided. If polychlorinated phenol congeners having a concentration of, for example, about 1–10 $\mu g/Nm^3$ is quantitatively analyzed, it is advisable that the concentration $N_S$ is set to 5 $\mu g/Nm^3$.

It can be considered that, in particular, in the case in which the isotope DDCP, DTCP or DTECP of DCP, TCP or TECP is used as an internal standard, the ionization efficiencies thereof are the same. Thus, the ratio k is one.

In the above-mentioned case, one kind of the internal standard is used to analyze polychlorinated phenol congeners consisting of di, tri, and tetrachlorophenols. However, in the case of plural materials to be quantitatively analyzed, an internal standard can be prepared for each of the plural materials. In this case, the above-mentioned formula can be represented by the following formula:

$$N_{CP}=k_{DCP} \cdot (I_{DCP1}/I_{S1}) \cdot N_{S1} + k_{TCP} \cdot (I_{TCP}/I_{S2}) \cdot N_{S2} + k_{TECP}(I_{TECP}/I_{S3}) \cdot N_{S3}$$

wherein the different internal standards are represented by subscripts 1, 2 and 3.

For example, dibromphenol, tribromophenol and tetrabromophenol are used as internal standards for DCP, TCP, and TECP, respectively.

In the case that the dependencies of ion strengths of a target trace gas and an internal standard upon the concentration of interfering components are different, DCP, TCP, TECP and the internal standard each of which has an experimentally-known concentration are used to obtain a correlation between the ion strengths of DCP, TCP and TECP and the ion strength of the internal standard when the concentration M of impurities changes. From this correlation, the concentration of the target trace gas can be obtained.

In other words, a correlation between the ion strengths in the following case is obtained: the case that temperature T, pressure P and the concentration of an internal standard are measured under the same conditions; the internal standard and each of DCP, TCP and TECP having a known concentration are simultaneously introduced into an ion source; and the concentration of hydrogen chloride are changed.

The following relationships can be approved:

$I_{DCP}=f_{DCP}(I_s)$, $I_{TCP}=f_{TCP}(I_s)$, and $I_{TECP}=f_{TECP}(I_s)$.

When the concentrations of DCP, TCP and TECP when this correlation has been obtained are represented by $N_{A,DCP}$, $N_{A,TCP}$, and $N_{A,TECP}$, respectively, the concentrations $N_{DCP}$, $N_{TCP}$, and $N_{TECP}$ of DCP, TCP and TECP in the case that the concentration of the interfering components in the flue gas has changed are represented by the following formulae:

$$N_{DCP}=N_{A,DCP} \times (I_{DCP}/f_{DCP}(I_s)),$$

$$N_{TCP}=N_{A,TCP} \times (I_{TCP}/f_{TCP}(I_s)), \text{ and}$$

$$N_{TECP}=N_{A,TECP} \times (I_{TECP}/f_{TECP}(I_s)).$$

The concentration $N_{CP}$ of the polychlorinated phenol congeners can be represented by the following formula:

$$N_{CP}=N_{DCP}+N_{TCP}+N_{TECP}.$$

The quantitative analysis using an internal standard additive has been described above, and the method of selecting an optimal internal standard additive will be described.

The internal standard additive is preferably a rare isotope of a target trace gas. In many case, however, a rare isotope is very expensive or is difficult to obtain. Thus, it is necessary to substitute a different substance for the isotope.

Atmospheric pressure chemical ionization or chemical ionization is greatly affected by other impurities, and is an ionization process which requires frequent calibrations. Since such ionization process has a simple step of ionization, it is easy to select an appropriate additive. Such a process advances according to the following steps. Ionization (primary ionization) is first caused by electrons generated by discharge or the like. The primary ionization is based on interaction between electrons having excessive energy and neutral molecules, and is unselective ionization. It is however said that subsequent collisions are caused about $10^5$–$10^6$ times in an atmospheric ion source or about $10^4$–$10^5$ times in a chemical ion source. By ion-molecule reaction or charge transfer reaction caused at this time, electrical charges are transferred to products which are more easily ionized (secondary ionization) As is presumed from such an ionization process, the secondary ionization is very selective. In such an ionization process, positive ions or negative ions are generated mainly by proton transfer reaction or charge transfer reaction. In order to decide an internal standard additive, it is necessary to assume the final step of the secondary ionization. For example, an aromatic molecule has a small ionization energy; thus, the molecule has a property of discharging electrons to turn to a positive ion (M+). A molecule having a high basicity, such as a molecule having an amino group, has a property of turning to a positive ion (M+1$^+$) by proton transfer reaction. A molecule having a large electron affinity, such as an aromatic nitro compound, has a property of attracting an electron to turn to a negative ion (M−). A substance having a high acidity, such as HCl, has a property of delivering a proton to another substance to turn to a negative ion (M−1$^-$). These can be simply estimated from the mass number and the ion electrical charge to be detected as compared with the original molecule (M).

The following will discuss a case in which 2,4-dichlorophenol is measured. When 2,4-dichlorophenol is measured in the negative mode of atmospheric pressure chemical ionization, an ion of (M−1$^-$) is detected. From this fact, it can be understood that this ionization is caused by the delivery of hydrogen. Thus, values obtained by subtracting the electron affinity of a dissociated molecule from a dissociating energy of a bond with hydrogen are compared as a parameter. This parameter is described "Mass spectrometer, Vol. 28, No.3, 185(1980)". As an actual parameter for phenol congeners, data described in Journal of the American Chemical Society, Vol. 99, No. 7, 2222 (1977) are referred to.

Referring to the drawings, an embodiment of the specific structure of the present invention (that is, a piping arrangement including a mass spectrometer in the case that an internal standard is added) will be described.

Figure 2:
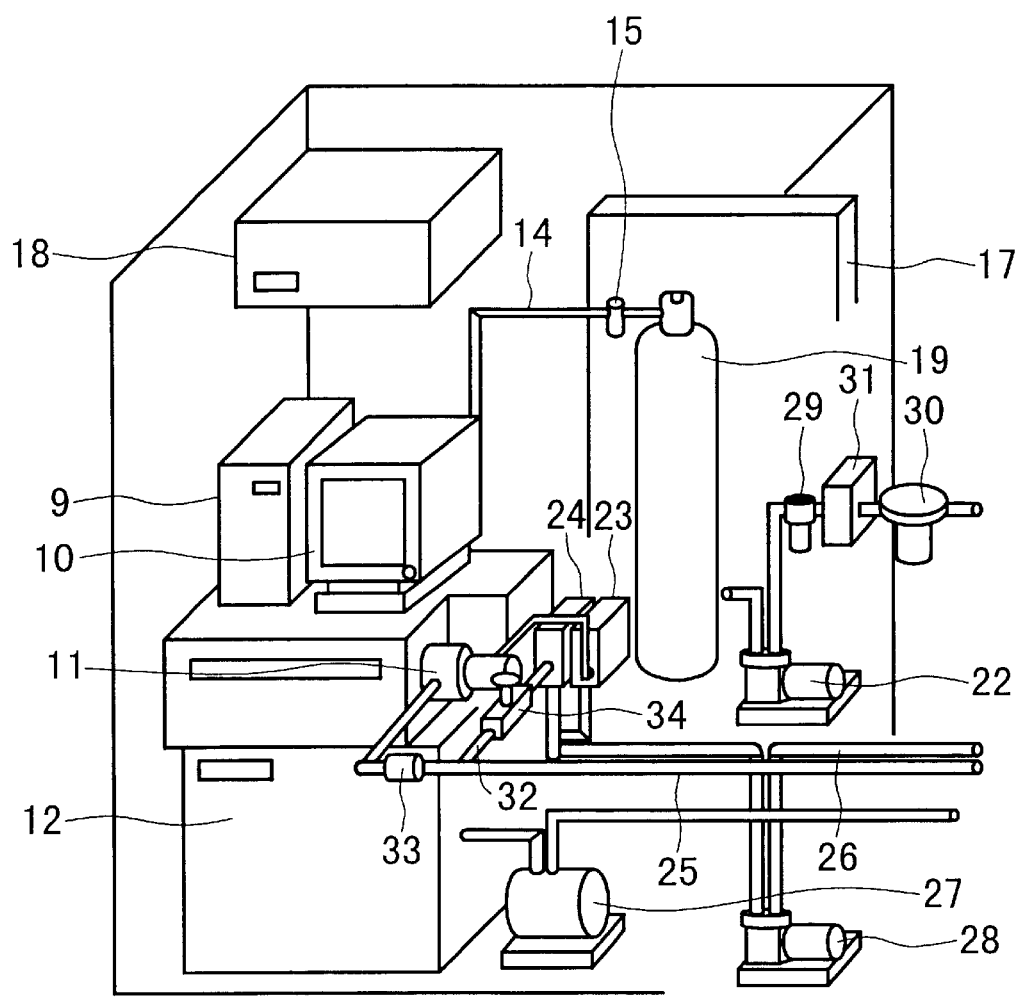
FIG. 2 is a view illustrating the exterior of the piping arrangement illustrated in FIG. 1.
Figure 3:
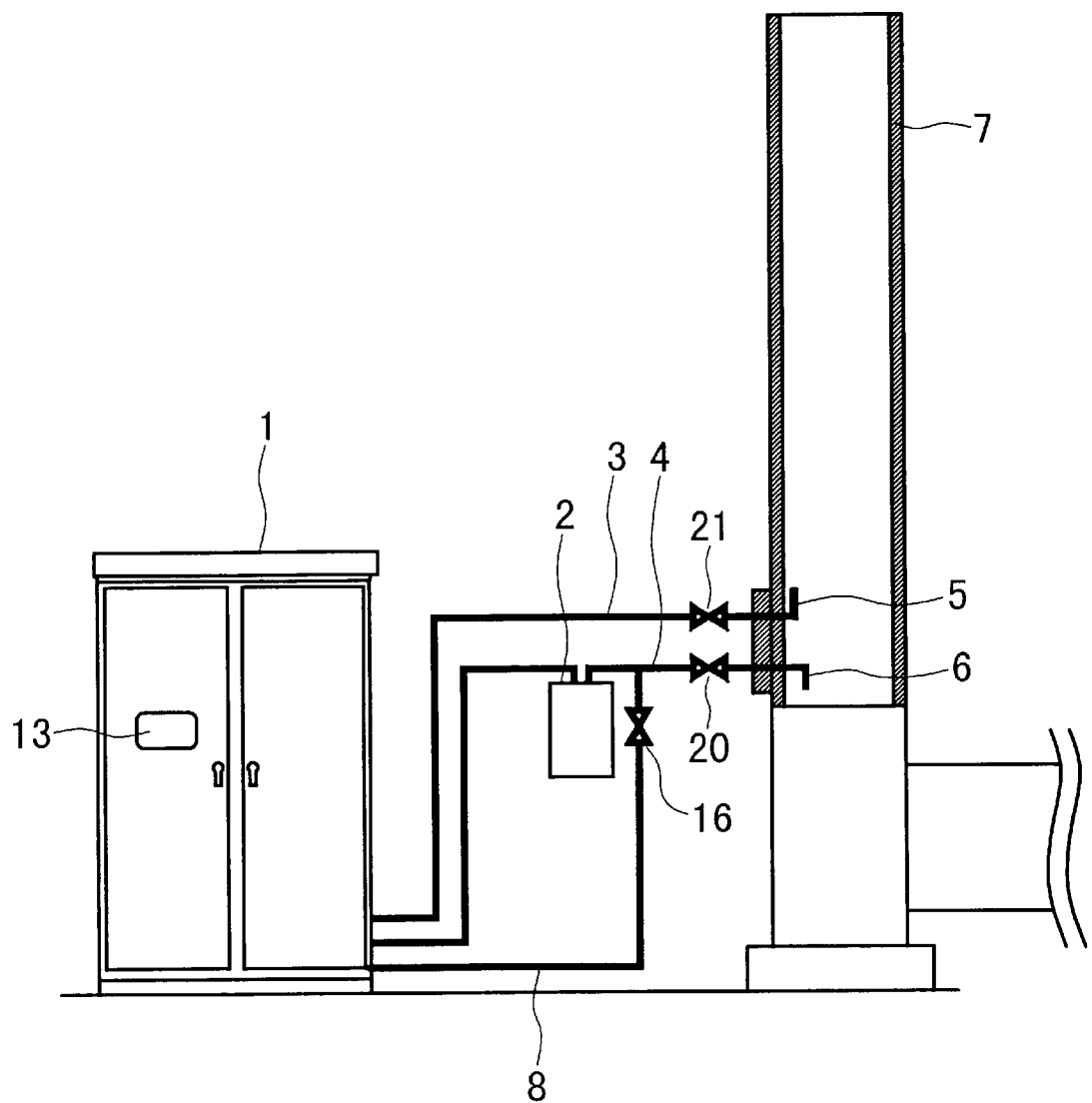
FIG. 3 is a schematic view illustrating the whole of the exterior of the piping arrangement illustrated in FIG. 1, including a flue gas duct.

FIG. 1 is a view illustrating a piping arrangement of an embodiment of the present invention. FIG. 2 is a view illustrating the exterior thereof, and FIG. 3 is a schematic view illustrating the whole of the exterior of the piping arrangement including a flue gas duct. A target trace gas is attracted from a flue gas duct 7 of a combustion furnace to an online measurement device 1 through a nozzle 6 and a pipe 4. The gas is absorbed with a pump 28 to introduce the gas into the online measurement device 1. The analyzed gas is discharged to the flue gas duct 7 through an flue gas return pipe 3. The gas absorbed from the flue gas duct 7 passes through the pipe 4, and fine particles called dust or mist are removed with a filter 2. Thereafter, the gas is introduced into the measurement device 1. From the atmosphere absorbed with a pump 22, duct is removed with a filter 29, and an internal standard gas is added to the upstream of the filter 2 through an internal standard vaporizer 30 and a pipe 8 connected thereto. Alternatively, the internal standard may be introduced with an air cylinder instead of the pump 22. The concentration of the internal standard is set up to a value similar to the average concentration of the target trace gas in flue gas which was beforehand measured by GC/MS or the like. If the concentration of polychlorinated phenol congeners is, for example, 1–10 $\mu g/Nm^3$ in measurement thereof in the flue gas duct, the concentration of the internal standard to be added is set to about 5 $\mu g/Nm^3$. In the case that a problem arises when the sample gas to which the internal standard is added is discharged into the flue gas duct, an activated carbon filter is set and the internal standard is caused to be absorbed thereon. Alternatively, the internal standard may be discharged into a furnace which can attain perfect combustion. It is advisable that the internal standard is put into a heat-resistant container which is made of a metal and has a hole having a diameter of about 0.1 mm to several mm, and the container is put into the internal standard vaporizer 30.

The shape of the internal standard vaporizer 30 may be any one if the generator 30 has a structure wherein the evaporated internal standard can be mixed with air from the pump 22. An example thereof is shown in FIG. 4A. The size and the shape of the hole of the container into which the internal standard is put may be decided in the manner that a target concentration can be generated dependently on the evaporated amount of the internal standard. In the case that there are plural target trace gases and plural internal standards are added accordingly, plural containers in which the plural internal standards are put are put into the internal standard vaporizer. Since the generation amount of the internal standard is greatly affected by temperature, it is important that the a heater is wound around the internal standard vaporizer 30 to control the temperature thereof into a constant value. In the case of preventing a phenomenon that the internal standard is filled into the piping by stopping the introduction of flue gas for a long time, for example, for maintenance, it is advisable that a branched pipe is set up as shown in FIG. 4B and the internal standard is returned by continuing to send the air.

In the mass spectrometer, it is sufficient that the gas flow rate is about 1–3 L(liter)/min. Therefore, a surplus flow is discharged through a bypass line 32. In order to remove finer dust from the gas introduced into an ionization section 11, a filter having a pore size of about 0.2 $\mu m$ is set up. Examples of the ionization section (ion source) 11 used in the mass spectrometer include ion sources using atmospheric pressure chemical ionization, chemical ionization, electron impact ionization, molecule ionization by plasma, and ionization by glow discharge. In the present embodiment, a counter flow type atmospheric pressure chemical ion source, which was developed by the present Applicant, is used. This ion source uses a method in which a target trace gas can be effectively ionized when a sample to be introduced into the ionization section is caused to flow conversely to the direction along which ions generated near a needle electrode advance by an electric field, that is, to flow toward the needle electrode. The flow rate of the sample toward the needle electrodes is set to 10 ml(milliliter)/min. or more.

A relationship between the concentration C1 measured in the ion source and the concentration C2 in the flue gas in the flue gas duct is as follows:

$$C2=C1\times(F2+F3+F4)/(F2+F3+F4-F1)$$

wherein the flow rate of the gas containing the internal standard is represented by F1, the counter flow rate of the gas flowing in the ion source is represented by F2, the flow rate of the gas flowing in the bypass is represented by F3, and the flow rate of the gas flowing from the ion source to the vacuum section of the mass spectrometer is represented by F4.

At this time, in connection with the flow rate F1, the concentration of the internal standard changes by a change in the amount of air flowing in the internal standard gas. Therefore, the flow rate of the air is preferably controlled into a constant value with a mass flow controller 31. When the counter flow rate F2 changes continuously, the ion efficiencies of the target trace gas and the internal standard in the ion source also change. Therefore, in order to make an accidental error at the time of calibration small, the flow rate F2 is preferably controlled into a constant value with a mass flow meter 23. It is necessary that the flow rate F2 of the flow toward the needle electrode is 10 ml/min. or more. The flow rate F4 may be estimated from the pore size and the length of the pore for taking in ions or may be beforehand obtained by experiments. The bypass flow rate F3 is measured with a mass flow meter and the flow rate F4 may be made to a constant value since the pressure of the ion source is controlled with a pressure control valve 34. Pressure signals for controlling the pressure control valve 34 are sent from a pressure sensor 35 (non-illustrated in FIG. 2) attached to the ion source.

The dust filter 2 is a filter into which metal elements having a length of several $\mu m$ are filled and can be suitably exchanged when it is blocked with ash or dust. To reduce absorption of the sample gas, it is necessary to raise the temperature of the wall of the dust filter 2 up to a higher temperature than the temperature of the pipe 4 for the sample gas. When the temperature of the pipe for the sample gas is about 120° C. in the case that dioxin precursors such as polychlorinated benzene and polychlorinated phenol are measured, it is effective that the temperature of the dust filter 2 is raised up to a high value of about 180 to 200° C. Many solid impurities or fly ash can be removed with the dust filter 2. If a metal filter is set up at the downstream thereof, inflow of finer dust into the ion source 11 can be prevented.

The size of the dust to be removed can be controlled by the size of the mesh of the metal filter. In many cases, a filter having a mesh of about 0.1 to 0.5 $\mu m$ is used. This part can be exchanged. Dependently on the amount of solid impurities or fly ash in the site where sample gas is collected, plural filters may be combined. If in this case the meshes of the filters are gradually made finer from the upstream of the pipes in this site to the downstream thereof, measurement for a long time can be attained. In order to prevent corrosion based on flue gas, it is preferable that the pipes and the valves are made of stainless steel or titanium, which is not easily corroded.

In order to prevent absorption of trace components of the walls of the pipes, it is preferable to use, as the pipes, polytetrafluoroethylene lining pipes or glass lining pipes. Instead of the glass lining pipes, glass tubes or quartz tubes cut into small sizes may be packed into pipes. There may be used a fused silica column having a wide bore, which is used as a column for gas chromatography (GC).

The sample gas is attracted with a pump 28 for introducing the sample gas, and is introduced into the ion source 11. The flow rate of the introduced sample gas depends on the inner size and the length of the used pipe for the sample gas, the air-sending speed of this pump 28, and so on. The flow rate is usually from about 1 to 300 L/min. As this pump 28, a mechanical pump such as a diaphragm pump may be used.

Dioxin and related compound thereto are present in only a minute amount in flue gas. These compounds are easily absorbed on the walls of the sample-collecting system, which are composed of the pipes, the filter and so on. In order to prevent such absorption as much as possible, the whole of the sample-collecting system is heated, or the pipes are made of a material having small absorption ability.

If the amount of flue gas flowing in the pipes is made large, the absorption can be reduced. That is, the retention time of the flue gas in the pipes is shortened as much as possible.

Considering that a mass spectrometer 12, a computer 9, a screen 10, and meters such as a flow controller are near the flue gas duct and outside rooms, they are set up inside a monitor rack highly sealed up, wherein the temperature thereof is controlled to some extent (about 10–50° C.) with an air-conditioner 18. Data obtained from measurement with the mass spectrometer 12 are transferred to a combustion control device or the like through signal lines and control lines. In this case, the mass spectrometer 12 may be made in such a manner that results on a CRT or a printer can be observed through a peep hole by the spectrometer 12 itself. By setting up the internal standard vaporizer 30, it is possible to subject the monitor section to a periodic inspection through a valve 16 for exchanging internal standards, and a pipe 8 for the internal standard. That is, the internal standard gas is introduced instead of flue gas, and then it is checked whether or not the amount of ions originating from the observed internal standard is more than a certain constant value. When the observed ion intensity is more than a constant value, maintenance is required. In the present invention, it is important that the internal standard is supplied at a constant concentration. Thus, it is preferable to check whether or not the concentration of the internal standard which is being added changes by GS/MS or the like.

Figure 5:
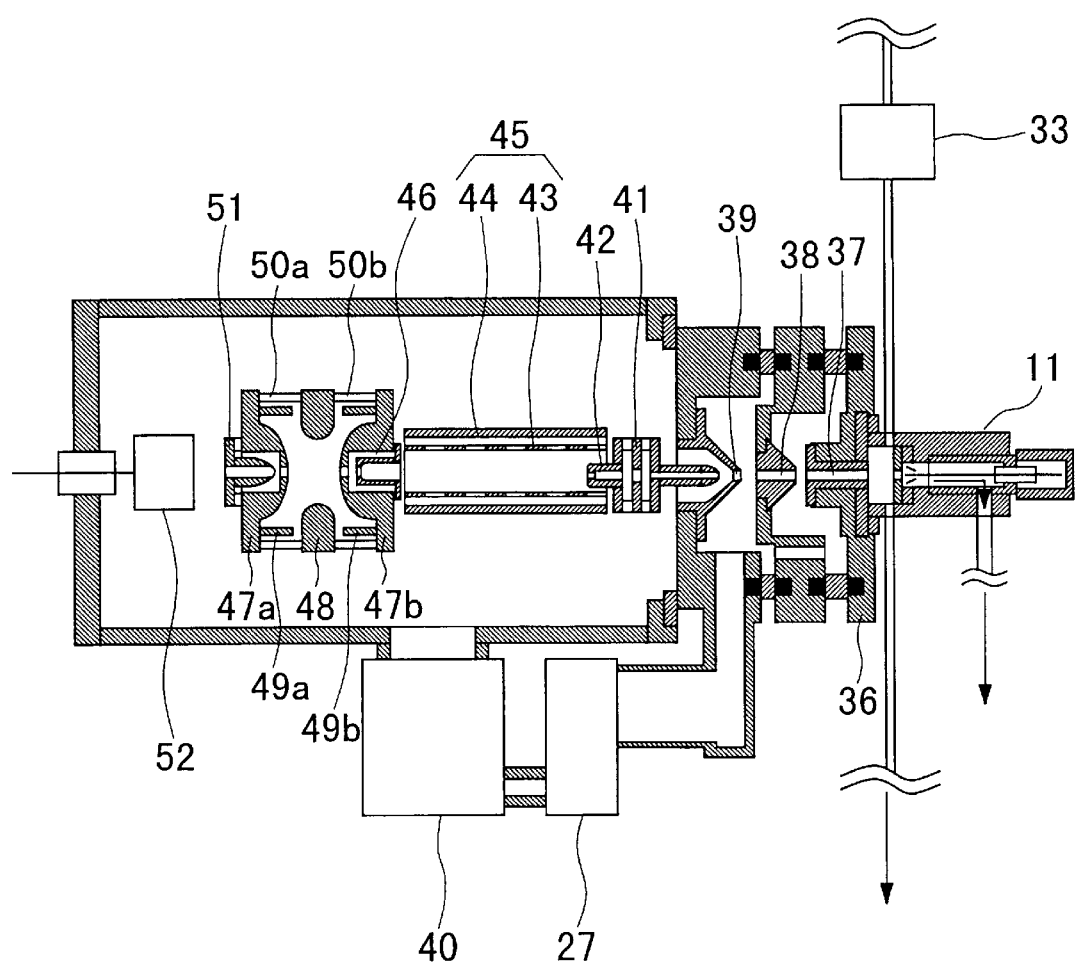
FIG. 5 is a sectional view illustrating an example of a mass spectrometer.

Referring to FIG. 5, the mass spectrometer 12 will be specifically described. When generated ions are analyzed, various kinds of mass spectrometers can be used. A case in which an ion trap mass spectrometer of ion accumulating type is used will be described hereinafter. The same description can be applied to cases in which other mass spectrometers (a quadruple mass spectrometer wherein mass separation is performed using the same high frequency electrical field, or a magnetic field type mass spectrometer using mass dispersion) are used.

Negative ions generated in the ion source of the present invention pass through a first ion taking-in pore 37 (diameter: about 0.3 mm, length: about 20 mm) made in a first flange-type electrode 36, a second ion taking-in pore 38 (diameter: about 0.6 mm, length: about 0.3 mm), and a third ion taking-in pore 39 (diameter: about 0.3 mm, length: about 0.3 mm), each of which is heated to 100–300° C. with a heater (not illustrated). Voltage can be applied between the first ion taking-in pore 37 and the second ion taking-ion pore 38, and between the second ion taking-in pore 38 and the third ion taking-ion pore 39. Thus, ion transmission ratio is improved and simultaneously cluster ions generated by adiabatic expansion are cleaved by collision with remaining molecules. In this way, ions of the sample molecules are generated. A differential pumping portion is usually evacuated with a roughing vacuum pump such as a rotary pump, a scroll pump, or a mechanical booster pump. This portion may also be evacuated with a turbo molecule pump. FIG. 5 illustrates a case in which a scroll pump 27 (pumping capacity: about 900 L/min.) and a turbo molecule pump 40 (pumping capacity: about 200–300 L/min.) are used for evacuations of the differential pumping portion and the mass spectrometer, respectively. The scroll pump 27 is also used as a pump for evacuating the back pressure side of the turbo molecule pump 40. The pressure between the second ion taking-in pore 38 and the third ion taking-ion pore 39 is from 0.1 to 10 Torr. A differential pumping portion using two pores (the first ion taking-in pore 37 and the third ion taking-ion pore 39) may be used. However, the flow rate of the flowing-in gas becomes larger than the above-mentioned case; therefore, a manner as follows is necessary: increase in the pumping speed of the used vacuum pump, separation of the pores, or the like. In this case, application of voltage between the two pores is also important.

The generated ions pass through the third ion taking-in pore 39, and subsequently the ions are converged into a convergent lens 41. As this convergent lens 41, a Einzel lens composed of three electrodes, or the like lens is used. The ions pass through an electrode 42 with a slit. The ions which have passed through the third ion taking-in pore 39 are converged into this slit through the convergent lens 41. Neutral particles or the like particles which are not converged collide with the vicinity of the slit so that these particles do not go easily toward the mass spectrometer. The ions which have passed through the electrode 42 with the slit are deflected and converged with a double cylindrical type lens 45 composed of an inner cylindrical electrode 43 and an outer cylindrical electrode 44. The double cylindrical type lens 45 causes deflection and convergence, using an electrical field of the outer cylindrical electrode which is spread out from the opening of the inner electrode. The details thereof is disclosed in JP-A-7-85834.

The ions which have passed through the double cylindrical type lens 45 are introduced into an ion trap mass spectrometer. The ion trap is composed of a gate electrode 46, end cap electrodes 47a and 47b, a ring electrode 48, shielding electrodes 49a and 49b, insulating rings 50a and 50b, and an ion taking-in lens 51. The gate electrode 46 has a function of preventing introduction of ions from the outside to the mass spectrometer when the ions trapped in the mass spectrometer are taken outside the mass spectrometer. The ions introduced into the ion trap mass spectrometer through the ion taking-in pore 39 collide with buffer gas, such as helium, introduced into the ion trap mass spectrometer so that the orbit of the ions becomes small. Thereafter, each of the ions having different mass numbers is discharged from the ion taking-in pore outside the ion trap mass spectrometer by scanning the high frequency voltage applied between the end cap electrodes 47a and 47b and the ring electrode 48. Each of the ions passes through the ion taking-in lens 51 and is then detected with an ion detector 52.

The pressure in the ion trap mass spectrometer when the buffer gas is introduced is from about $10^{-3}$ to $10^{-4}$ Torr. The ion trap mass spectrometer is controlled by a mass spectrometer control unit. The ion trap mass spectrometer has a property of trapping ions. Thus, ore of good points of the ion trap mass spectrometer is that even a small concentration of the sample can be detected if the time for trapping ions is extended. Accordingly, even when the concentration of the sample is small, ions can be concentrated high times in the ion trap mass spectrometer. Thus, pretreatment of the sample, such as concentration thereof, can be made very simple.

In the case that as the sample gas supplied from the sample line a stable isotope is used, the reduction ratio based on reaction or absorption in the filter 2 or the pipes in the middle, and the ionization efficiency and detection efficiency in the mass spectrometer 12 are equal. Therefore, such a case is very effective for systems in which absorption onto the pipes is greatly caused. However, the stable isotope is usually expensive. Thus, a problem about costs may arise.

Figure 6:
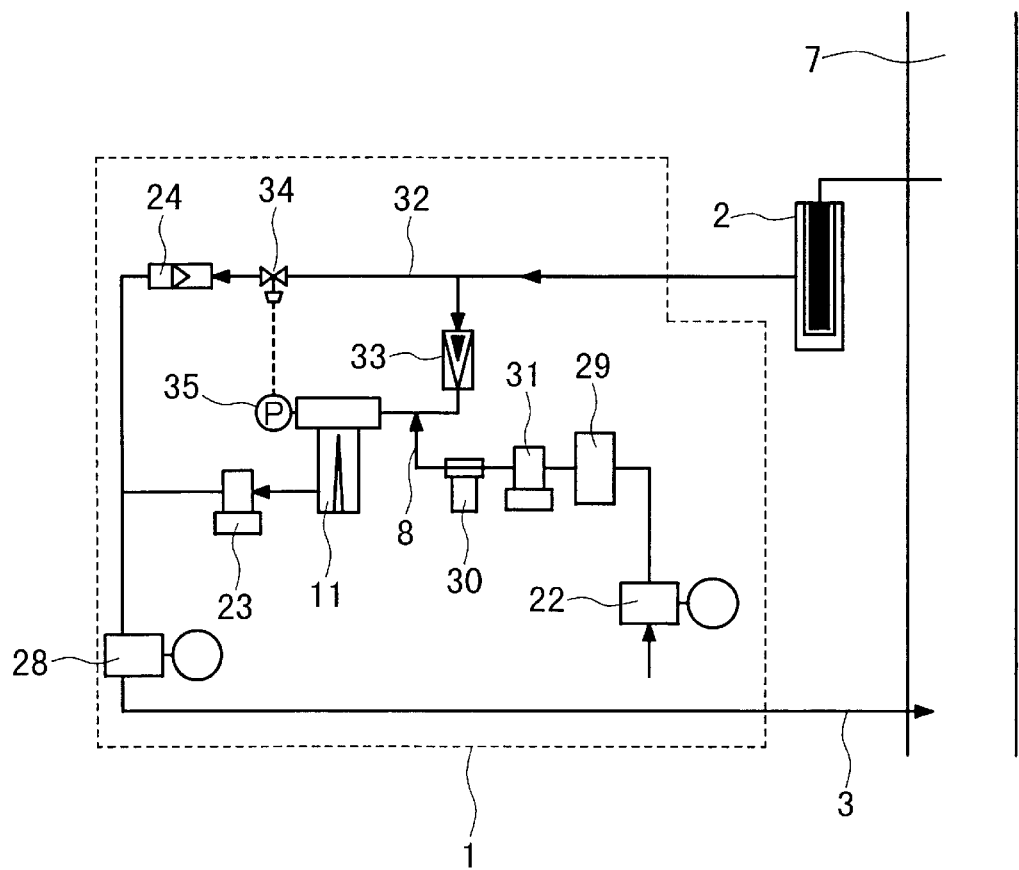
FIG. 6 is a view illustrating a piping arrangement of another embodiment of the present invention.

On the other hand, in the case that the reduction ratio on the filter or the pipes is small, or the ratio can be regarded as substantially constant during the measurement, there is known a method of adding an internal standard just before the ion source 11 as illustrated as another embodiment in FIG. 6. It is advisable to select, as the internal standard, a substance having substantially the same ionization step and ionization efficiency as a target trace gas, and causing the generation of ion having different mass numbers.

Figure 7:
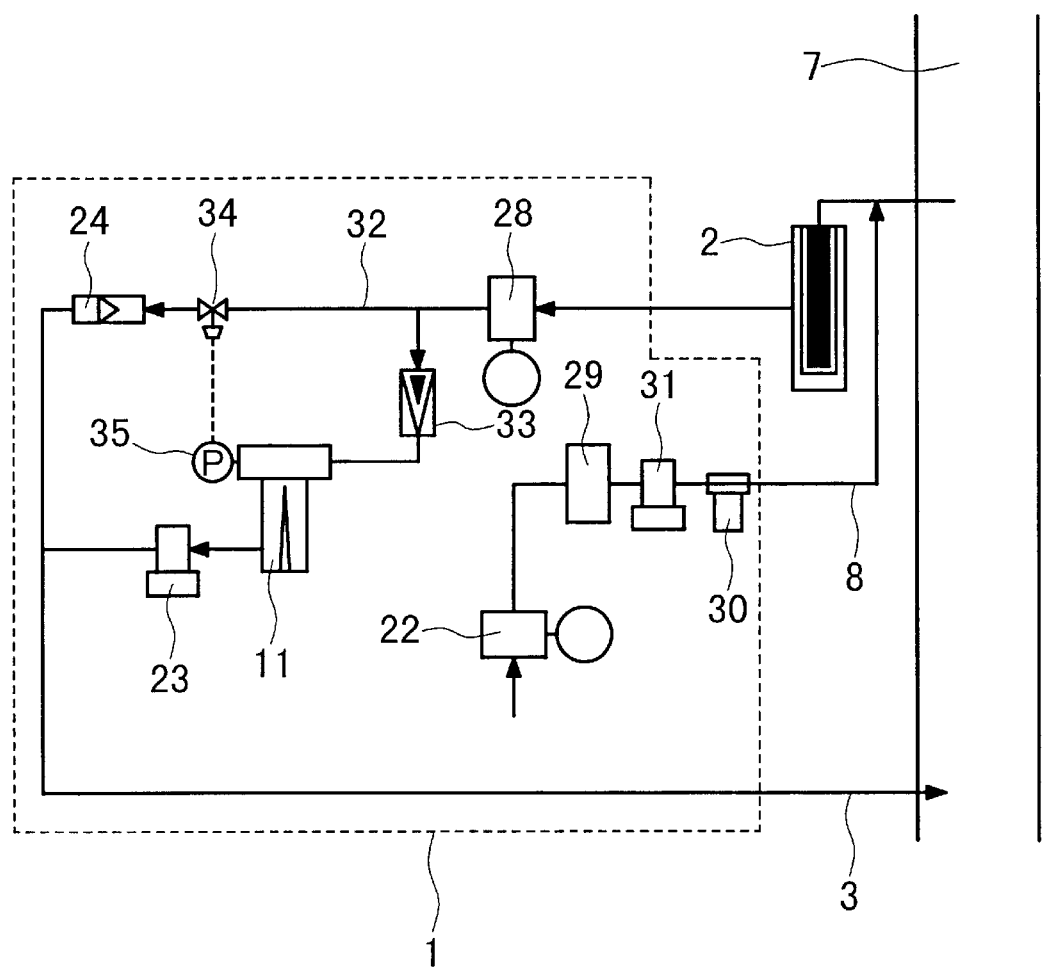
FIG. 7 is a view illustrating a piping arrangement of a further embodiment of the present invention.

In the piping arrangements illustrated in FIGS. 1 and 6, the method for introducing flue gas from the flue gas duct 7 to the taking-in ion source is a method of absorbing the flue gas with the pump 28 arranged at the downstream side of the ion source. However, in the case that gas discharged from the pump does not hinder the measurement (for example, mass-number overlap is not caused, and sensitivity is not lowered) and a target trace gas does not adhere to the inside of the pump so that ion strength of the generated ions is not lowered, it is allowable to set up the pump 28 between the ion source and the flue gas duct, and pump out and introduce the flue gas from the flue gas duct to the ion source, as illustrated as a further embodiment in FIG. 7. In this case, the pressure in the ion source is higher than in the above-mentioned case in which the flue gas is absorbed into the ion source. Therefore, the ion strength of the generated ions becomes large. It is advisable that an oilless pump having high-temperature resistance is used as the pump 28 to prevent absorption and degassing.

Figure 8:
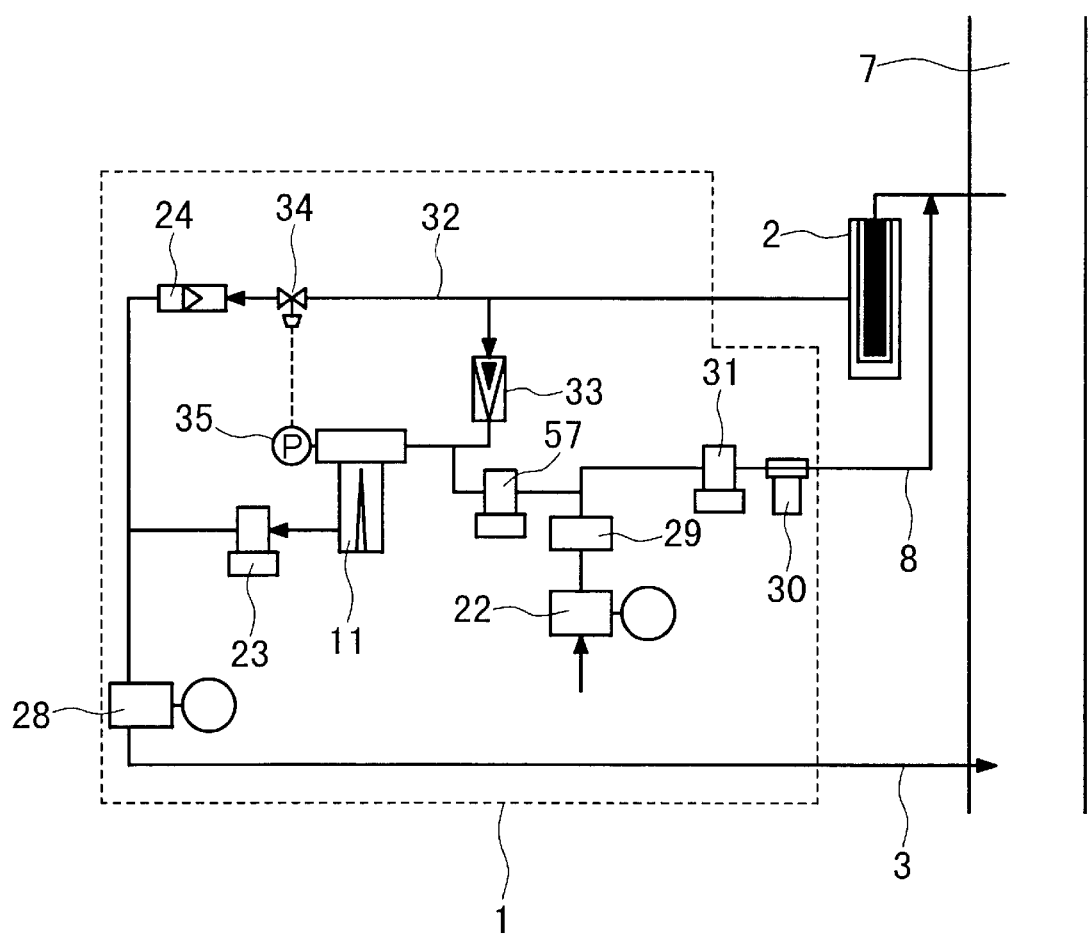
FIG. 8 is view illustrating a piping arrangement of a still further embodiment of the present invention.
Figure 9:
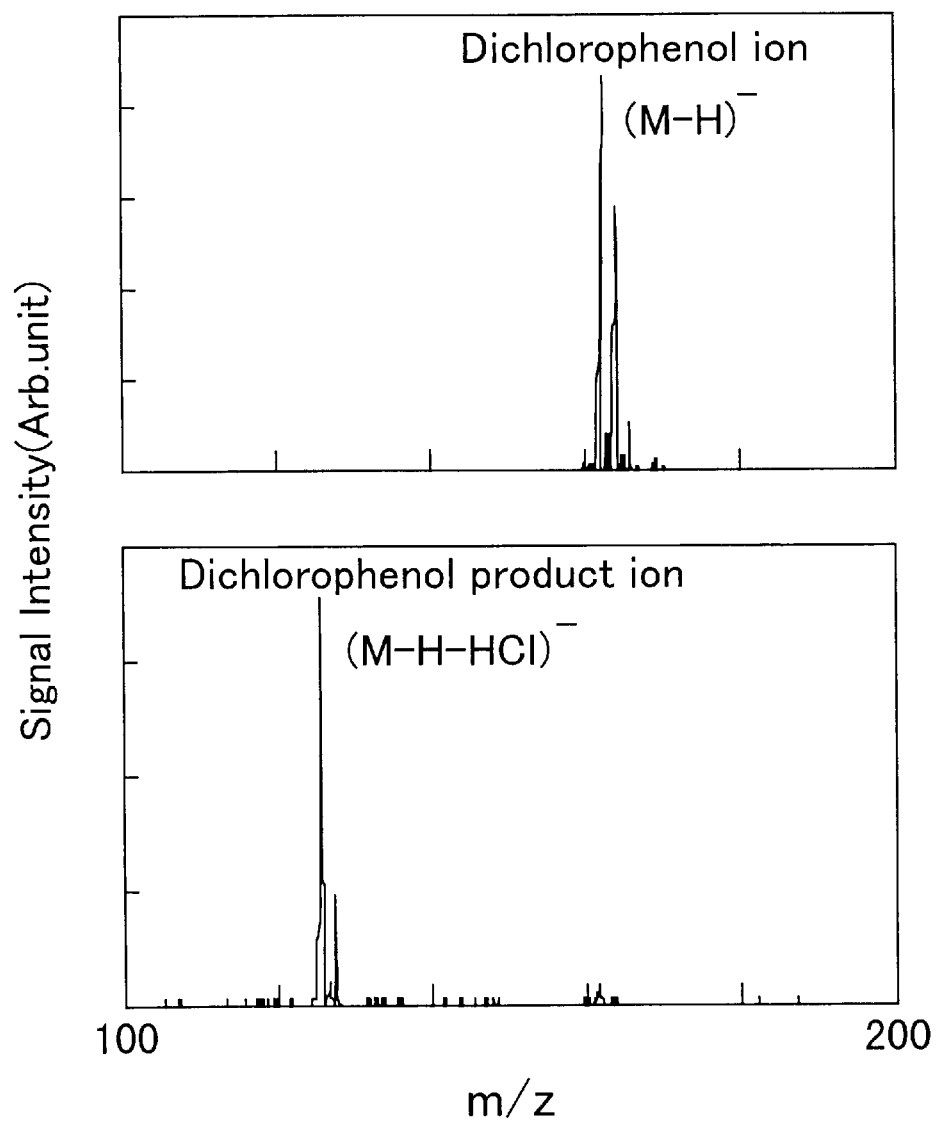
FIG. 9 is a characteristic graph showing a measurement result according to the present invention.

In the case that the concentration of impurities is high so that the sensitivity to a target trace gas drops remarkably and measurement accuracy deteriorates, air whose flow rate is controlled is introduced into the inlet of the ion source to dilute flue gas, as illustrated as a still further embodiment in FIG. 8. In this way, the effect of the impurities can be weakened. In this case, the target trace gas is also diluted. Therefore, it is necessary to mind that the flue gas is diluted not to exceed the detection limit of the device.

The following will describe the sequence of the measurement of the present invention. In the case that flue gas is subjected to gas analysis, ions of impurities (chemical noises) having the same mass number as a target trace gas may be contained in the flue gas. This causes an accidental error in quantitative analysis. That is, the measured value becomes larger than a true value. In this case, multi-step mass spectrometry (MS/MS) is used to separate the ions of the impurities from the ions of the target trace gas. If MS/MS is used in the case that the target trace gas is dichlorophenol, the target trace gas is decomposed to ions of dichlorophenol-decomposition products and ions of impurities. Thus, the molecular ion quantity originating from dichlorophenol can be measured. In the case of trichlorophenol or tetrachlorophenol, it cannot be decomposed. Therefore, ions of impurities are decomposed and them the strength of the remaining ions which have not been decomposed is measured to analyze the ion quantity of trichlorophenol or tetrachlorophenol.

Figure 10:
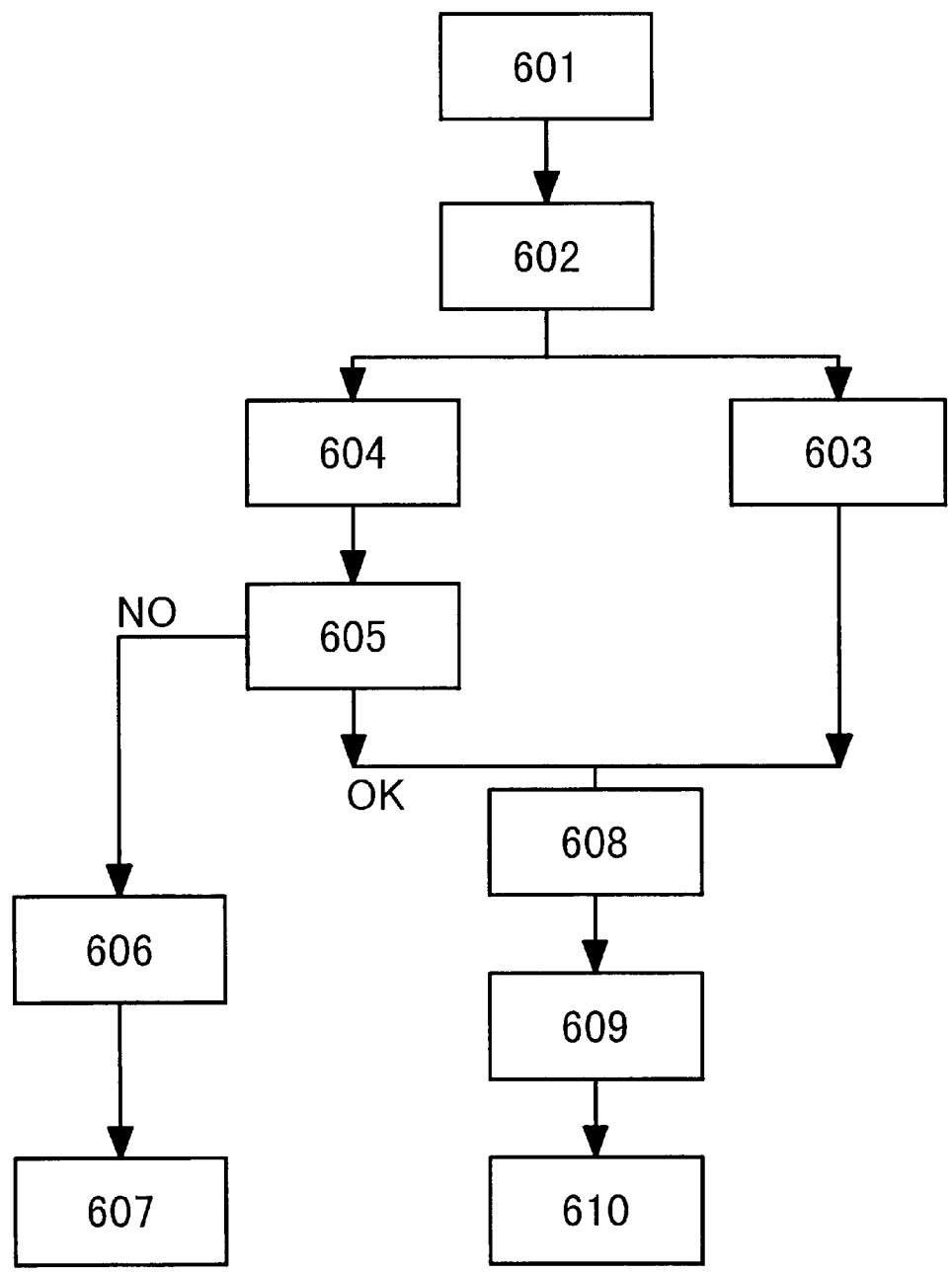
FIG. 10 is a flowchart for showing an example of measurement sequence in the present invention.

Referring to FIG. 10, one example of the sequence of the measurement of the present invention will be described. A measurement is started (step 601). Thereafter, MS spectra or MS/MS spectra are analyzed (step 602) to measure the ion strength of a target trace gas (step 603) and measure the ion strength of an internal standard (step 604). In order to check whether the ion source 11 and the mass spectrometer 12 work normally, it is checked whether the ion strength of the internal standard drops or rises extremely (step 605). In the case that it is abnormal, a warning is issued (step 606), and a necessary maintenance is done (step 607). In the case that it is normal, the ion strength ratio of the target trace gas to the internal standard is measured (step 608) when the internal standard is an isotope of the target trace gas. Thereafter, the ratio is multiplied by the concentration of the internal standard that was beforehand measured, to calculate the concentration of the target trace gas (step 609). In the other cases, the concentration of the target trace gas is calculated from a correlation between the target trace gas and the internal standard which was beforehand obtained (step 609). After the calculation of the concentration and display thereof, the following measurement will be started (step 610).

In the case that the present device is used as a monitor for measuring flue gas, the present device self-diagnoses whether an abnormality breaks out in measured signals, background, or the temperature, pressure or flow rate of the flue gas, or the like during online measurement or, if necessary, one time per day. Thereafter, necessary steps such as automatic washing, automatic calibration, issue of the warning "the device is abnormal", or stop of the device are taken.

Figure 11:
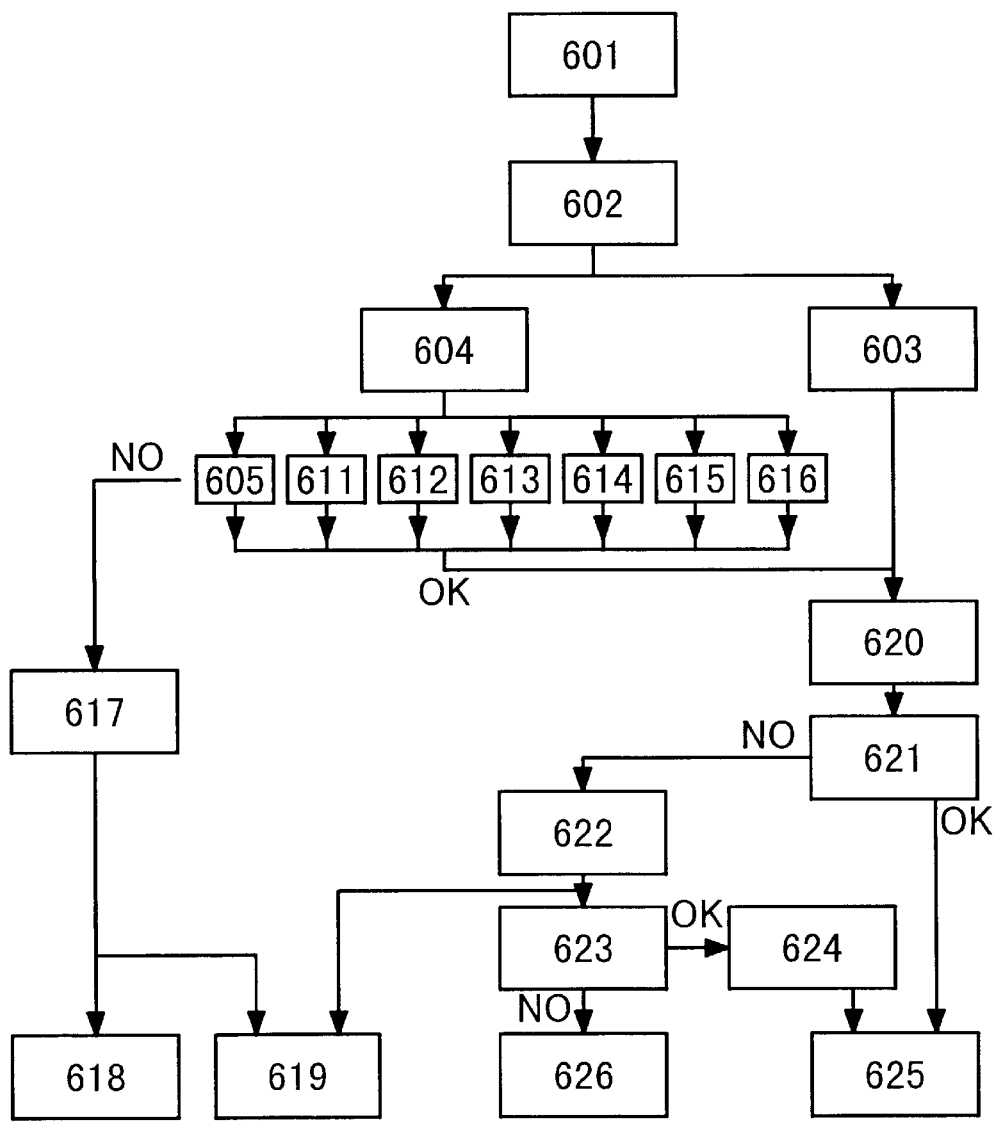
FIG. 11 is a flowchart for showing another example of measurement sequence in the present invention.

In order to know a sudden abnormal state, another process is necessary. FIG. 11 shows one example of the sequence of the measurement in this case. According to this sequence, it can be checked whether a caused abnormality is routine or sudden. The sequence up to the measurement of the ion strength of a target trace gas (step 603) and the measurement of the ion strength of an internal standard (step 604) is the same as shown in FIG. 10. The ion strength of the internal standard is checked (step 605). Moreover, the vacuum degree of the mass spectrometer, the values of the respective flow meters, the temperature of the piping, the temperature inside the monitor, the current of corona discharge, and the strength of all ions are checked (steps 611, 612, 613, 614, 615 and 616), respectively. When an abnormality arises, a warning is issued (step 617) and a necessary maintenance is done (step 618). For the check of the abnormality, an average value in the incineration plant is manually set up beforehand. Alternatively, it is allowable to repeat measurement and obtain an average automatically. When the abnormality arises, components which give an abnormal value may be contained in the flue gas. Therefore, the device is changed into a measurement mode different from normal monitoring (step 619). Upon the abnormality, mass spectrometric analysis may be performed with the mass spectrometer to obtain a mass spectrum and record it together with other parameters in a file. This helps research of a cause of the abnormality.

When any abnormality does not arise, dioxin congeners, polychlorinated benzene congeners and polychlorinated phenol congeners are subjected to sequential measurements (step 620). The value of each of these components is compared with the average value (step 621). If the resultant deviation is larger than a given value, a warning is issued outside (step 622) and then an automatic diagnoses is made (step 623). Calibration is made (step 624), and then the next measurement is started (step 625). When the outbreak of an abnormality is recognized by the automatic diagnosis, a high-rank warning is issued to stop the monitor device (step 626). As values for issuing the warning, high and low values may be set up. When the measured value exceeds the low value, only a lamp is turned on for caution. When the measured value rises further and exceeds the high value, the lump is turned on and in addition thereto a buzzer is sounded as an alarm. Such a monitoring system is used not only for the check of the concentrations of the components in the flue gas which is being measured, but also for checks of the ion strength of the internal standard , the vacuum degree of the mass spectrometer, the values of the respective flow meters, the temperature of the piping, the temperature inside the monitor, the current of corona discharge, and the strength of all ions (steps 605, 611, 612, 613, 614, 615 and 616), respectively. About, for example, the vacuum degree of the mass spectrometer, it is possible to integrate a system wherein a lamp for caution is turned on when the vacuum degree is slightly shifted (raised or lowered) from a normal degree and the device is stopped when the vacuum degree is further shifted. Exchange of the filter in the needle electrode or the piping or maintenance thereof (such as cleaning thereof) becomes necessary one time per several months. Working time of the present device is measured in a data processing unit, and the information "maintenance is needed after a certain hour" may be displayed on its screen.

If mass spectra are constantly obtained and recorded not only upon the outbreak of an abnormality but also during the monitoring by integrating a mass spectrum scanning step into a cycle for monitoring dioxin congeners or the like, the state of the incineration plant can be grasped at all times. Ions of water make their appearance as a large peak in a mass spectrum, for example, if a great deal of watery rubbish is burned. Ions of chlorine make their appearance as a large peak in a mass spectrum if a great deal of vinyl chloride is burned. If observation of a mass spectrum is periodically taken in during the monitoring of trace components and this mass spectrum is monitored, the state of an abnormality can be grasped. The measured mass spectrum is compared with an average mass spectrum measured on an earlier occasion (comparative mass spectrum) If a new mass peak makes its appearance or a large mass peak disappears, it is acknowledged that an abnormality breaks out. That is, the strengths of the same peaks of m/z (the ratio of mass to the number of charges) on two mass spectra for comparison are subjected to subtraction. If no peaks are present on the mass spectra, the strength is regarded as zero. If a large peak makes its appearance on the subtraction spectrum, this is based on a component which makes its appearance suddenly on the flue gas. Therefore, a warning is issued outside to inform appearance of an abnormal component.

The measured data are processed in a data processing unit. The data are filed and recorded together with set values of combustion conditions, measured values and so on. To sites where a value over a standard value is exhibited, color such as red or pink is displayed. In this way, a warning is issued to a watchman. The data are output to a printer or a CRT if necessary. The data are sent to a combustion monitor/control system.

In the case that dioxin congeners, polychlorinated phenol congeners or chlorobenezene congeners in flue gas are measured, it is effective that negative corona discharge is used to detect the target trace gas as a negative ion. As an index compound indicating the combustion state of an incineration furnace, chain-form hydrocarbons are also used. In this case, it is effective to use positive corona discharge in order to detect the hydrocarbons. When the ion strength ratios between the detected hydrocarbons are measured and the hydrocarbons having a large mass number are detected at a high level, it can be considered that the state of combustion is imperfect. Therefore, if any one of positive discharge and negative discharge is changed to the other at regular intervals (for example, at intervals of several minutes) to change any one of measurement of the hydrocarbons and measurement of dioxin congeners, polychlorinated phenol congeners or polychlorinated benzene congeners to the other, the state of combustion in the incineration furnace can be more specifically grasped.

Figure 12:
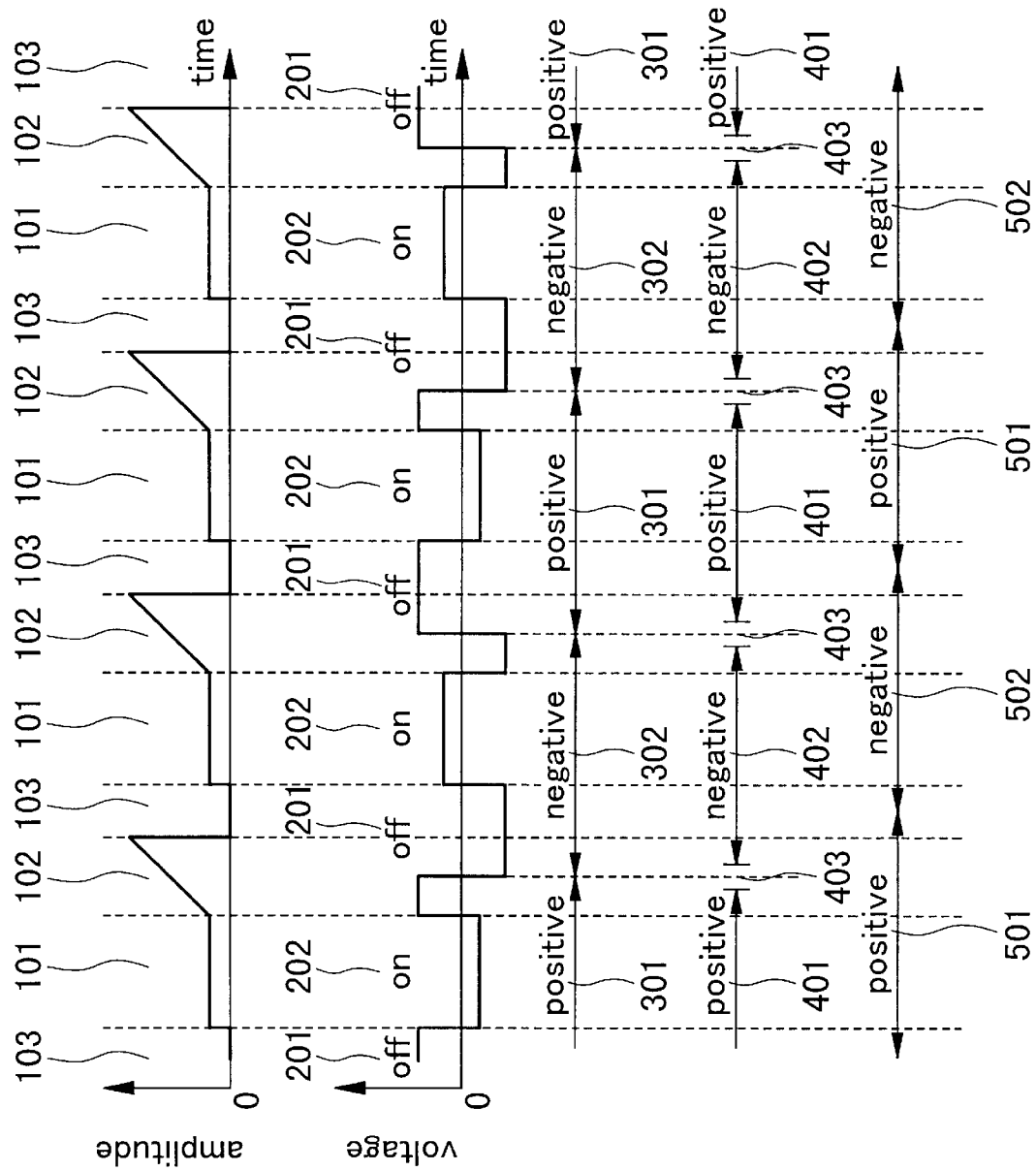
FIG. 12 is a view for explaining a mode of taking in positive and negative ions in an ion source section in the present invention.

The following will describe a specific method for changing any one of positive (+) and negative (−) discharges to the other in the ion source. FIG. 12 illustrates one example of a mode of taking in positive and negative ions.

As illustrated in FIG. 12, in synchronization with amplitudes (101, 102, 103) of high frequency waves applied to the ring electrode [see (a)], the following are changed: ionization modes (401, 402) of the ion source [see (d)]; ion transmission modes (301, 302) of the ion optics [see (c)]; and ion detection modes (501, 502) of the detector [see (e)]. About the voltage applied to the gate electrode [see (b)], an ion transmission interval 201 and an ion shielding interval 202 are alternatively set up. The polarity of the applied voltage is reversed dependently on the ionization mode.

As described above, the positive ion- and negative ion-analyzing modes is alternatively used. In this way, data on positive ions and negative ions can be obtained by one measurement operation. To reverse the polarity of ions to be measured, the polarity of voltages applied to the ion optics (composed of the ion source, the ion orbit converging lens and so on), the detector and so on must be reversed. For example, in the above-mentioned counter flow type atmospheric pressure chemical ion source developed by the present Applicant, a high voltage is applied to its needle electrode and opposite electrode. In a positive ion measuring mode, a positive voltage is applied to the needle electrode. In a negative ion measuring mode, a negative voltage is applied to the needle electrode. In the same way, the polarity of voltages applied to the ion optics and the detector must be reversed dependently on the polarity of ions to be measured.

About these parts where polarity should be reversed, especial attention should be paid to the change of the ionization mode of the ion source. In the positive ion measuring mode, a positive voltage of several kV is applied to the needle electrode, and in the negative ion measuring mode, a negative voltage of several kV is applied thereto. Immediately after the polarity of the voltage applied to the needle electrode is reversed, the generation of ions becomes unstable. Careful investigations have not been made on the time from the reversion of the polarity to the stabilization of the generation of ions. If the time is presumed from experience up to now, the time is about 0.05 second. Therefore,if the ionization mode is changed in a remaining ion removing interval 103 after a series of operations for obtaining a mass spectrum, that is, an ion trapping interval 102 and a mass separation interval 102, a waiting time for some time is necessary. To reduce this waiting time, it is advisable to change the mode of the ion source in the mass separation interval 102, as shown in FIG. 12. The change of the ion optics and the reversion of the polarity of the gate voltage are preferably synchronized with the change of the ionization mode of the ion source. However, the ionization mode of the ion source is not immediately changed. Preferably, therefore, an ion generation stopping interval 403 is set up when the ionization mode of the ion source is changed, and in this ion generation stopping interval 403 the ion optics are changed and the polarity of the gate voltage is reversed. It is advisable that the voltage at the detector is reversed in the ion trapping interval 101 or in the remaining ion removing interval 103. This is because ions are detected in the mass separation interval 102. As illustrated in FIG. 12, a positive ion detecting interval 501 and a negative ion detection interval 502 are alternatively arranged.

As described above, the mode of the ion source can be changed and the polarity of the gate voltage or the ion optics can be reversed in the mass separation interval 102 or the remaining ion removing interval 103. The change and reversion are desirably synchronized. The mode of the detector can be changed in the ion trapping interval or the remaining ion removing interval 103. The point that attention should be paid about the whole of the device including pipes of the sample collection system is that flue gas is caused to flow into the atmospheric ion source, the pipes and so on at all times during measurement to keep the exchange of the gas and materials absorbed on the walls into an equilibrium state and lose absorption of trace components on the walls. When the flow of flue gas is stopped for the stop of the incineration furnace, the maintenance thereof or the exchange of filters in the sampling system, high-purity nitrogen gas or the like is caused to flow automatically to prevent stains on the atmospheric ion source and the pipes. Purge gas such as high-purity gas is caused to flow dependently on stains on the atmospheric ion source and the pipes, for example, one time per week. When the sending-out of the internal standard from the internal standard vaporizer 30 is stopped in the monitoring device illustrated in FIG. 1 and so on, nitrogen gas sent from a nitrogen gas cylinder (not illustrated) flows through the valves to the pipes, and the atmospheric chemical ion source 11, so as to wash them. By causing nitrogen gas to flow at the time of start or stop of the device or flow periodically in the middle of measurement, the device can be cleaned up. The high-purity nitrogen gas may be introduced into the sample collecting pipe 4, separately from the internal standard sample introducing system. In the case that pure nitrogen is introduced into the introducing system and subsequently flue gas is introduced to start measurement, the flue gas is caused to flow continuously for 30 minutes or more to prevent absorption on the walls of the pipes.

Figure 13:
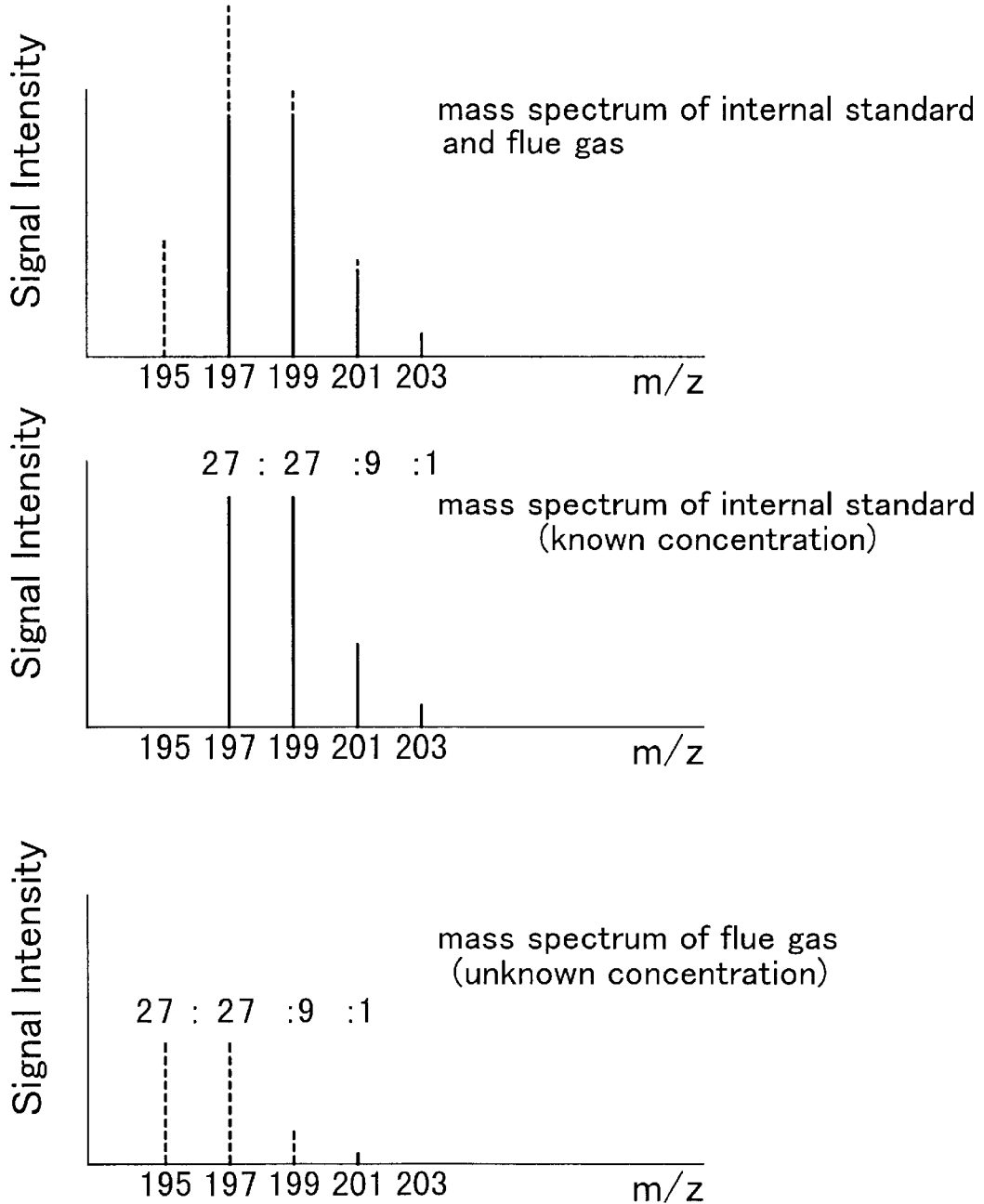
FIG. 13 is a graph for explaining an example of quantitative analysis according to the present invention.

FIG. 13 shows one example of quantitative analysis wherein a target trace gas is trichlorophenol and an internal standard is a deuterium hydrogen substituted isotope of trichlorophenol (an isotope obtained by substituting two hydrogen on the benzene ring with deuterium hydrogens, the mass number of which increases by 2).

Trichlorophenol, which is to be measured, has 3 chlorine atoms. An isotope of chlorine having a mass number of 35, and an isotope thereof having a mass number of 37 are present at a ratio of 3:1. Therefore, a spectrum wherein at sites having mass numbers of 195, 197, 199 and 201, relative strengths are 27, 27, 9 and 1, respectively, is detected. On the other hand, peaks of the isotope whose mass number increases by 2 are detected at sites having mass numbers of 197, 199, 201 and 203. The relative strengths thereof are the same as above. Thus, the peaks overlap at the sites of the mass number of 197, 199 and 201.

In other words, each of peaks actually measured is detected as the sum of the strength of the target trace gas and that of the internal standard (the isotope). The concentration of trichlorophenol and the ratio α of the ion strengths thereof would be equal to the concentration of the isotope and the ratio α of the strengths thereof. When the concentration of the trichlorophenol to be measured is represented by (unknown) Cx and the concentration of the isotope is represented by (known) Cy, the ion strength (In) at each of the mass numbers can be represented by the following equation:

$$In = \alpha \times (Cx \times \beta x + Cy \times \beta y)$$

wherein β is the ratio of peaks at the site having each of the mass numbers.

Since unknown numbers are two numbers, i.e., Cx and α, two mass numbers about which chemical noises are less and sensitivity is high are selected from the 4 peaks and then a simultaneous linear equation is solved. Thus, Cx can be obtained. In the case that an isotope of dichlorophenol or tetrachlorophenol is used as an internal standard, an calibration can be made in the same way.

In the case that a 13 substituted isotope of trichlorophenol (an isotope obtained by substituting Cs (i.e., carbons) on the benzene ring with 13Cs, the mass number of which increases by 6) is used, only its peak at the mass number of 201 overlaps with a peak of polychlorinated phenol in flue gas. About the isotope, therefore, the peak at the mass number of 203 is analyzed, and about trichlorophenol in the flue gas the peak at the mass number of 195 or 197 is analyzed. They are compared, and an calibration can be made. When the mass number of the isotope for the calibration overlaps with the mass number of each of the components contained in the flue gas, an accidental error is generated at the time of the calibration. Thus, another isotope should be used. No problems arise in the case that they can be separated by MS/MS.

As described, according to the present invention, as an calibration means for online monitoring using mass spectrometry, a substance having a similar ionization efficiency, for example, a rare isotope is added at a constant concentration as an internal standard. The ion quantity thereof is measured. In this way, the concentration of a target trace gas in gas containing impurities can be calibrated while being continuously calibrated. Thus, high-accuracy analysis can be made.

As a result, dioxin and related compounds contained in combustion flue gas resulting from incineration of non-industrial waste and industrial waste, exhaust gas from metal refining processes, exhaust gas from cars, or the atmosphere are detected. In this way, the concentration of the dioxin congeners and the related compounds such as dioxin precursors can be measured at a high accuracy and at a real time. Furthermore, monitored results can be used for optimal control of combustion. As a secondary result, mechanisms such as complex valves become unnecessary since an internal standard gas for calibration is caused to flow continuously. Thus, reduction in costs can be expected.

What is claimed is:

1. A combustion control system comprising:

a sampling nozzle for sampling a gas, including a target material gas to be analyzed;

a filter which removes a small particle from the sampled gas;

a sample introduction tube which connects together said sampling nozzle and said filter;

means for adding continuously an internal standard gas at a known constant concentration to the sampled gas in said sample introduction tube, wherein the internal standard gas has a chemical property similar to the target material gas and has substantially the same ionization efficiency as the target material gas;

means for introducing the sampled gas and the internal standard gas, at the same time, into an atmospheric pressure chemical ionization source; for ionizing the target material gas and the internal standard gas, at the same time;

a mass spectrometer for subjecting respective ions, generated in the atmospheric pressure chemical ionization source from the target material gas and the internal standard gas, to mass spectrometry and measuring electrical signals from the respective ions;

a data processing unit for calculating the ion intensity ratio between the target material gas in the sampled gas and the internal standard gas from the measured electrical signals to analyze, continuously, the concentration of the target material gas quantitatively in real time; and means for controlling combustion of an incineration furnace based on the concentration of the target material gas.

2. A monitoring device for analyzing a sample, comprising:

a sampling nozzle which is disposed in a flue for sampling a flue gas including a target material gas to be analyzed;

a filter which removes a small particle from the sampled gas;

a sample introduction tube which connects together said sampling nozzle and said filter;

means for adding continuously an internal standard gas at a known constant concentration to the sampled gas in said sample introduction tube, wherein the internal standard gas has a chemical property similar to the target material gas and has substantially the same ionization efficiency as the target material gas;

means for introducing the sampled gas and the internal standard gas, at the same time, into an atmospheric pressure chemical ionization means for ionizing the target material gas and the internal standard gas, at the same time;

a mass spectrometer for subjecting respective ions generated from the target material gas and the internal standard gas to mass spectrometry; and a data processing unit for processing results-of the mass spectrometry, wherein the data processing unit is made to continuously analyze the target material gas quantitatively in real time by calculating the ion signal intensity ratio of the target material gas to the internal standard gas.

3. A monitoring device according to claim 2, wherein the internal standard has substantially the same ionization efficiency as the target material.

4. A monitoring device for analyzing a sample, comprising:

a sampling nozzle which is disposed in a flue for sampling a flue gas including a target material gas to be analyzed;

a filter which removes a small particle from the sampled gas;

a sample introduction tube which connects together said sampling nozzle and said filter;

means for adding continuously an internal standard gas at a known constant concentration into the sampled gas in said sample introduction tube, wherein the internal standard gas has a chemical property similar-to the target material gas and has substantially the same ionization efficiency as the target material gas, and the internal standard gas is a substance resulting from replacement of at least one element constituting the target material gas by isotope thereof;

means for introducing the sampled gas and the internal standard gas, at the same time, into an atmospheric pressure chemical ionization means for ionizing the target material gas and the internal standard gas, at the same time;

a mass spectrometer for subjecting respective ions generated from the target material gas and the internal standard gas to mass spectrometry; and a data processing unit for processing results of the mass spectrometry, wherein the data processing unit is made to continuously analyze the target material gas quantitatively in real time by calculating the ion signal intensity ratio of the target material gas to the internal standard gas.

5. A monitoring-device for analyzing a sample, comprising:

a sampling nozzle which is disposed in a flue for sampling a flue gas containing a target material gas to be analyzed and impurities;

a filter which removes a small particle from the sampled gas;

a sample introduction tube which connects together said sampling nozzle and said filter;

means for adding continuously an internal standard gas at a known constant concentration to the sampled gas in said sample introduction tube, wherein the internal standard gas and the target material gas have substantially the same rate of change of ionization efficiency due to concentration fluctuations of the impurities in an atmospheric pressure chemical ionization means, and has substantially the same ionization efficiency as the target material gas;

an atmospheric pressure chemical ionization means for ionizing the target material gas and the internal standard gas, at the same time;

a mass spectrometer for subjecting respective ions generated from the target material gas and the internal standard gas to mass spectrometry; and a data processing unit for processing results of the mass spectrometry, wherein the data processing unit is made to continuously analyze the target material gas quantitatively in real time by calculating the ion signal intensity ratio of the target material gas to the internal standard gas.

* * * * *